United States Patent
Choi et al.

(10) Patent No.: US 9,529,434 B2
(45) Date of Patent: Dec. 27, 2016

(54) PRESENTATION DEVICE AND METHOD FOR OPERATING THE DEVICE

(71) Applicant: SAMSUNG ELECTRONICS CO., LTD., Suwon-si (KR)

(72) Inventors: Chang Mok Choi, Seoul (KR); Sang Joon Kim, Hwaseong-si (KR); Sang Kon Bae, Seongnam-si (KR); Seung Keun Yoon, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 14/161,145

(22) Filed: Jan. 22, 2014

(65) Prior Publication Data

US 2014/0368424 A1 Dec. 18, 2014

(30) Foreign Application Priority Data

Jun. 17, 2013 (KR) .......................... 10-2013-0068878

(51) Int. Cl.
*G06F 3/01* (2006.01)
*G01C 21/36* (2006.01)
*G06F 3/0488* (2013.01)
*A61B 5/0488* (2006.01)

(52) U.S. Cl.
CPC .............. *G06F 3/015* (2013.01); *G01C 21/367* (2013.01); *G01C 21/3664* (2013.01); *G06F 3/0488* (2013.01); *A61B 5/04888* (2013.01); *G01C 21/3676* (2013.01); *G06F 2203/04806* (2013.01)

(58) Field of Classification Search
CPC ............ G06F 3/015; G06F 3/02; G06F 3/048; G06F 3/041; G09G 5/00; G09G 5/373
See application file for complete search history.

(56) References Cited

U.S. PATENT DOCUMENTS

| 8,291,341 B2 * | 10/2012 | Tseng et al. .................. 715/786 |
| 2006/0017692 A1* | 1/2006 | Wehrenberg et al. ........ 345/156 |
| 2006/0061544 A1 | 3/2006 | Min et al. |
| 2006/0121958 A1 | 6/2006 | Jung et al. |
| 2010/0031186 A1 | 2/2010 | Tseng et al. |

(Continued)

FOREIGN PATENT DOCUMENTS

| EP | 2 741 176 A2 | 6/2014 | |
| IL | WO 2011/055326 * | 5/2011 | ............. G06F 15/00 |

(Continued)

OTHER PUBLICATIONS

Extended European Search Report issued Oct. 29, 2014 in counterpart European Patent Application No. 14160911.5 (10 pages, in English).

*Primary Examiner* — Andrew Sasinowski
(74) *Attorney, Agent, or Firm* — NSIP Law (57) ABSTRACT

A presentation device and an method of operating the presentation device may quickly move to a desired area on a map by adjusting a level of an electromyographic (EMG) signal even though a range of a motion of an arm is limited when searching the map using a wearable mobile device. The presentation device includes a first sensor unit configured to contact a measurement target and to obtain an electromyographic (EMG) signal from the measurement target; and a display controller configured to control a field of view (FOV) window for displaying a map area based on the EMG signal.

23 Claims, 7 Drawing Sheets

(56) References Cited

U.S. PATENT DOCUMENTS

| | | |
|---|---|---|
| 2011/0115822 A1 | 5/2011 | Bae |
| 2011/0148755 A1 | 6/2011 | Lee et al. |
| 2012/0098769 A1 | 4/2012 | Nagasaka |
| 2012/0274593 A1* | 11/2012 | Chiang .................... 345/173 |
| 2013/0002724 A1 | 1/2013 | Heinrich et al. |

FOREIGN PATENT DOCUMENTS

| | | |
|---|---|---|
| JP | 2005-011037 | 1/2005 |
| KR | 10-2006-0069985 | 6/2006 |
| KR | 10-0812245 | 3/2008 |
| KR | 10-2009-0032208 | 4/2009 |
| KR | 10-2011-0062558 | 6/2011 |
| KR | 10-2011-0062563 | 6/2011 |
| KR | 10-2012-0073830 | 7/2012 |
| WO | WO 01/27735 A1 | 4/2001 |
| WO | WO 2011/055326 A1 | 5/2011 |
| WO | WO 2012/095919 A1 | 7/2012 |

\* cited by examiner

EMG SIGNAL = 0

FIG. 3B

EMG SIGNAL = 10

PRESENTATION DEVICE AND METHOD FOR OPERATING THE DEVICE

CROSS-REFERENCE TO RELATED APPLICATIONS

This application claims the benefit under 35 U.S.C. §119 (a) of Korean Patent Application No. 10-2013-0068878, filed on Jun. 17, 2013, in the Korean Intellectual Property Office, the entire disclosure of which is incorporated herein by reference for all purposes.

BACKGROUND

1. Field

The following description relates to a presentation device method for operating the presentation device.

2. Description of Related Art

Currently, smart phones and new wearable mobile devices are being widely used. In such wearable mobile device, even though a user does not view a smart phone, information obtained through the smart phone over a wireless data network is visualized on a separately provided screen. The smart phone may have a relatively large screen, and may process information in response to the user touching and manipulating a screen. The wearable mobile device may have a relatively small screen compared to the screen of the smart phone. Therefore, when the user touches the wearable mobile device's screen, the screen may be mostly occluded by the finger, and thus may not be accurately controlled.

The wearable mobile device may be controlled using a voice recognition. However, the precision and efficiency of voice recognition may diminish in a noisy environment. An EMG signal sensed from a body and a gesture of the body may control an external device in detail and more efficiently.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, there is provided a presentation device, including a first sensor unit configured to contact a measurement target and to obtain an electromyographic (EMG) signal from the measurement target; and a display controller configured to control a field of view (FOV) window for displaying a map area based on the EMG signal.

The display controller may be configured to adjust a speed of the FOV window on a map in response to a magnitude of the obtained EMG signal.

The display controller may be configured to adjust a speed of the FOV window associated with a second map area that does not include the displayed map area to be greater than a speed of the FOV window associated with the displayed map area.

The presentation device may include a second sensor unit configured to obtain an acceleration signal by sensing a motion of the measurement target, wherein the display controller is configured to move the FOV window toward a direction identified by the acceleration signal.

The display controller may be configured to adjust a zooming speed of the FOV window in response to a magnitude of the obtained EMG signal.

The display controller may be configured to adjust a zooming speed of the FOV window associated with displaying a map area that includes the displayed map area to be greater than a zooming speed of the FOV window associated with displaying a portion of the displayed map area.

The presentation device may include a second sensor unit configured to obtain an acceleration signal by sensing a motion of the measurement target, wherein the display controller is configured to increase or decrease a size of a map area associated with the FOV window, based on a direction identified by the acceleration signal.

The first sensor unit may be configured to obtain the EMG signal generated in response to at least one of a muscular contraction or a muscular relaxation of the measurement target.

The map area may be displayed on a display unit.

In another general aspect, there is provided a method of operating a presentation device, the method including obtaining an electromyographic (EMG) signal from a measurement target using a first sensor unit in contact with the measurement target; and controlling a field of view (FOV) window to determine a map area to be displayed based on the EMG signal.

The controlling the FOV window may include controlling the FOV window by adjusting a speed of the FOV window on a map in response to a magnitude of the obtained EMG signal.

The controlling the FOV window may include controlling the FOV window by adjusting a speed of the FOV window associated with a second map area that does not include the displayed map area to be greater than a speed of the FOV window associated with the displayed map area.

The method may include obtaining an acceleration signal by sensing a motion of the measurement target, using a second sensor unit, wherein the controlling the FOV window comprises controlling the FOV window by moving the FOV window toward a direction identified by the acceleration signal.

The controlling the FOV window may include controlling the FOV window by adjusting a zooming speed of the FOV window in response to a magnitude of the obtained EMG signal.

The controlling the FOV window may include controlling the FOV window by adjusting a zooming speed of the FOV window associated with displaying a map area that includes the displayed map area to be greater than a zooming speed of the FOV window associated with displaying a portion of the displayed map area.

The method may include obtaining an acceleration signal by sensing a motion of the measurement target, using a second sensor unit, wherein the controlling the FOV window comprises controlling the FOV window by increasing or decreasing a size of a map area associated with the FOV window based on a direction identified by the acceleration signal.

In another general aspect, there is provided a presentation device, including a first sensor unit configured to contact a measurement target and to obtain an electromyographic (EMG) signal from the measurement target; a second sensor unit configured to obtain an acceleration signal by sensing a motion of the measurement target; and a display controller configured to control a field of view (FOV) window for displaying a map area based on at least one of the EMG signal or a direction identified by the acceleration signal.

The display controller may be configured to move the FOV window at a predetermined speed.

The display controller may be configured to control the FOV window to display a second map area that is greater than the displayed map area in response to a upward motion of the measurement target.

The display controller may be configured to control the FOV window to display a second map area that is smaller than the displayed map area in response to a downward motion of the measurement target.

The presentation device may be a mobile device.

The mobile device may include a display unit configured to display the map area.

The presentation device may be a wearable smart device.

Other features and aspects will be apparent from the following detailed description, the drawings, and the claims.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

A sensor unit may refer to a sensor or a set of sensors attached to a measurement target. The sensor unit may be in contact with the measurement target to obtain a signal from the measurement target or to sense a motion of the measurement target. For example, the sensor unit may include one or more of an optical sensor, a piezoelectric sensor, a force sensor, a mechanomyogram (MMG) sensor and an electromyographic (EMG) sensor. The sensor unit may be attached to any part of a body where muscles for generating a signal, such as an EMG signal, are present, such as, for example, wrist, arm, face, leg, head, and neck. The sensor unit may obtain a signal, such as an EMG signal, generated in response to a muscular contraction and a muscular relaxation. Such a sensor unit is referred to as a first sensor unit.

As another example, the sensor unit may include a gyroscope, a geomagnetic field sensor such as a magnetometer, a global positioning system (GPS) sensor, and an acceleration sensor such as an accelerometer to obtain an acceleration signal about a motion of a body by directly or indirectly monitoring a motion of the body. Such sensor unit is referred to as a second sensor unit.

A presentation device according to a non-exhaustive example may navigate to a map area displayed on a display unit in a direction identified by an acceleration signal obtained at the second sensor unit. The presentation device may control a speed of moving the map area based on a magnitude of the EMG signal obtained at the first sensor unit. Accordingly, even when the motion of an arm is limited, the presentation device may quickly navigate to an area not visible on a map by controlling a level of the EMG signal.

As a non-exhaustive illustration only, the presentation device 100 described herein may refer to mobile devices such as, for example, a cellular phone, a smart phone, a wearable smart device (such as, for example, a ring, a watch, a pair of glasses, a bracelet, an ankle bracket, a belt, a necklace, an earring, a headband, a helmet, a device embedded in the cloths or the like), a personal computer (PC), a tablet personal computer (tablet), a phablet, a personal digital assistant (PDA), a digital camera, a portable game console, an MP3 player, a portable/personal multimedia player (PMP), a handheld e-book, an ultra mobile personal computer (UMPC), a portable lab-top PC, a global positioning system (GPS) navigation, and devices such as a high definition television (HDTV), an optical disc player, a DVD player, a Blue-ray player, a setup box, or any other device capable of wireless communication or network communication consistent with that disclosed herein. In a non-exhaustive example, the wearable device may be self-mountable on the body of the user, such as, for example, the watch, the glasses, or the bracelet. In another non-exhaustive example, the wearable device may be mounted on the body of the user through an attaching device, such as, for example, attaching a smart phone or a tablet to the arm of a user using an armband, or hanging the wearable device around the neck of a user using a lanyard.

Figure 1:
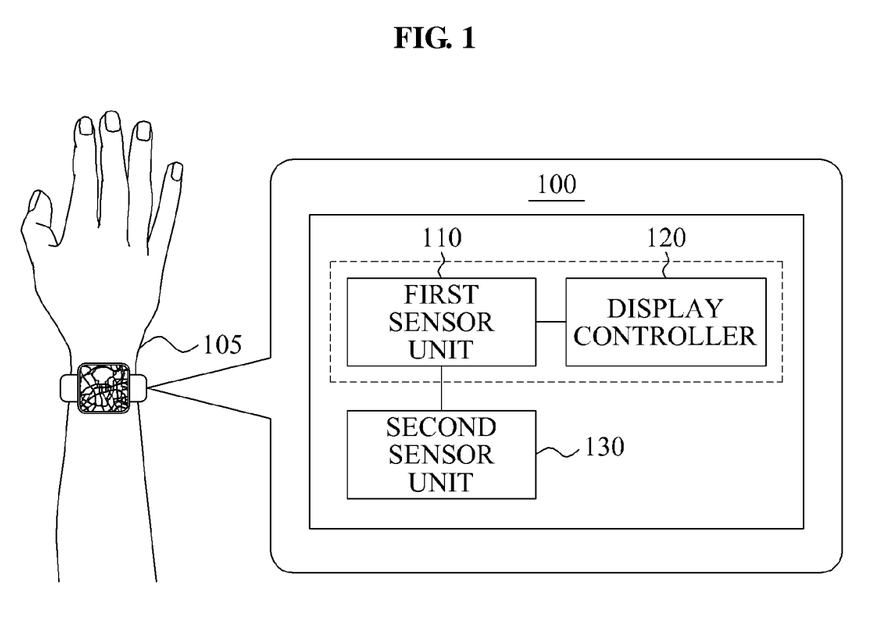
FIG. 1 is a diagram illustrating an example of a presentation device.

FIG. 1 is a diagram illustrating an example of a presentation device 100. Referring to FIG. 1, the presentation device 100 may include a first sensor unit 110 and a display controller 120. The presentation device 100 may further include a second sensor unit 130.

The first sensor unit 110 contacts the measurement target 105 to obtain an EMG signal from the measurement target 105. The first sensor unit 110 may obtain an EMG signal generated in response to at least one of a muscular contraction or a muscular relaxation of the measurement target 105. For example, when the measurement target 105 is the wrist of a user, the first sensor unit 110 may sense an EMG signal generated in response to a muscular contraction and a muscular relaxation of the wrist. The measurement target 105 may be any portion of a body where muscles for generating an EMG signal are present, such as, for example, wrist, arm, face, leg, head and neck of the body.

The first sensor unit 110 may include at least one sensor configured to sense a signal, such as an EMG signal from muscles of the measurement target 105 and may monitor the contraction or relaxation of muscles using the at least one sensor. The first sensor unit 110 may include, for example, optical sensor, a piezoelectric sensor, a force sensor, an MMG sensor, and an EMG sensor to obtain an EMG signal. The EMG signal may include, for example, a bioelectric/magnetic signal, a bio-impedance signal, and a biomechanical signal.

In a non-exhaustive example, the first sensor unit 110 may be fixed to a wrist member, such as a wrist band, which is attached to the measurement target 105. A sensing surface of the first sensor unit 110 may be fixed to the wrist member such that it is in direct contact with the measurement target 105. The sensing surface may be a surface where at least one EMG sensor is disposed. The sensing surface may contact the measurement target 105 to sense an EMG signal generated from the measurement target 105. For example, the wrist member may sense the measurement target's 105 EMG signals, such as bioelectric/magnetic signals, bio-impedance signals, and biomechanical signals, using the first sensor unit 110.

The wrist member may be in contact with the skin covering the muscles of the wrist and the wrist member may surround the entire wrist. In this example, the sensing surface of the wrist member may be spread throughout the wrist member. Accordingly, using at least one EMG sensor, the first sensor unit 110 may collect EMG signals from the muscles of the entire wrist that is the measurement target 105.

The display controller 120 may control a field of view (FOV) window for determining a map area to be displayed on a display unit using an EMG signal. The FOV window may be a virtual frame used to designate a map area to be displayed on the display unit. The display unit may be implemented as a liquid crystal display (LCD), a light-emitting diode (LED) display, a plasma display panel (PDP), a screen, a terminal, and the like. A screen may be a physical structure that includes one or more hardware components that provide the ability to render a user interface and/or receive user input. The screen can encompass any combination of display The display may be a single-screen or a multi-screen display. A single physical screen can include multiple displays that are managed as separate logical displays permitting different content to be displayed on separate displays although part of the same physical screen. The display controller 120 may determine the map area to be displayed on the display unit by navigating the FOV window on the map.

For example, the display controller 120 may adjust a speed at which the FOV moves on the map to be in proportion to a magnitude of the obtained EMG signal. When an EMG signal having a relatively larger magnitude is obtained within a short period of time, the display controller 120 may control the FOV window to move quickly on the map in proportion to the magnitude of the obtained EMG signal. When an EMG signal having a relatively smaller magnitude is obtained over a long period of time, the display controller 120 may control the FOV window to move slowly on the map. The movement of the FOV window on the map may be at a predetermined speed.

The display controller 120 may adjust a moving speed of the FOV window associated with a second map area not currently displayed on the display unit to be greater than a moving speed of the FOV window associated with a first map area currently displayed on the display unit. For example, the display controller 120 may control the FOV window to move quickly to the second map area, which is distant from the area currently displayed on the map. Accordingly, a map search on the distant area may be efficiently performed. The display controller 120 may control the FOV window to move slowly in the first map area, which is closer to an area on the map. Accordingly, a detail map search on the near area may be supported.

Figure 2A:
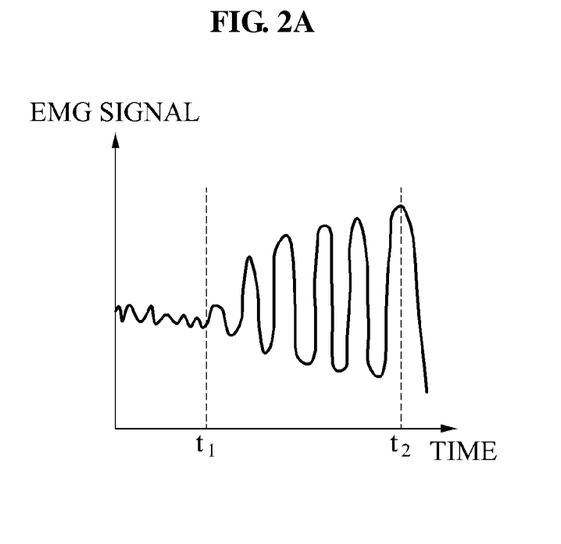
FIGS. 2A through 2C are diagrams illustrating examples of controlling a moving speed of a field of view (FOV) window based on a magnitude of an electromyographic (EMG) signal.
Figure 2B:
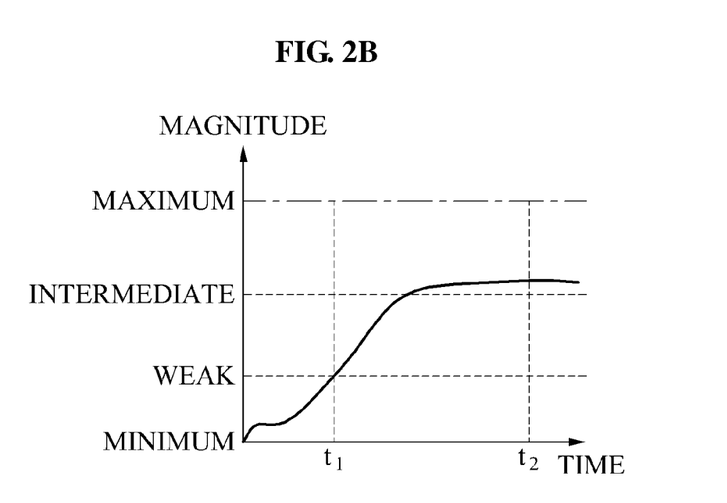
Figure 2C:
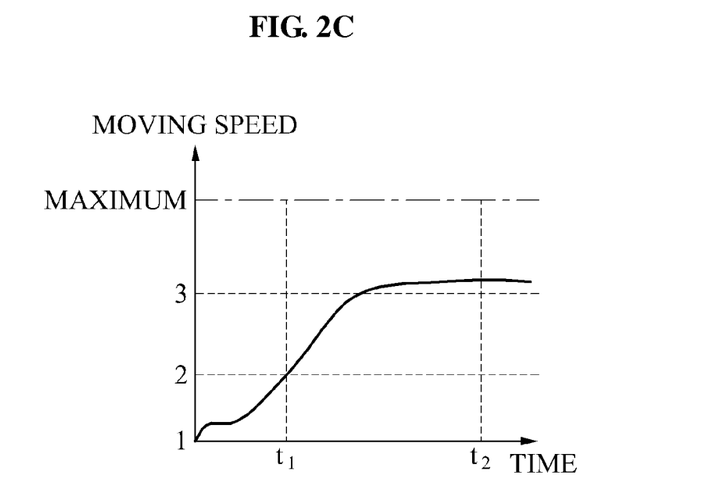

FIGS. 2A through 2C are diagrams illustrating examples of controlling a moving speed of a FOV window based on a magnitude of an EMG signal. FIG. 2A illustrates an EMG signal obtained at the first sensor unit 110 of the presentation device 100. As illustrated in FIG. 2A, an EMG signal is obtained in a form of an analog sine wave. For example, an EMG signal may have a relatively great wavelength between time periods of $t_1$ to $t_2$ during which a strain is applied to a finger.

FIG. 2B illustrates a comparison of a magnitude of an EMG signal by performing signal processing. For example, based on EMG signals of FIG. 2A, the display controller 120 may generate a graph of a secondary curve having a suddenly rising tilt after t1 in which the wavelength increases. The display controller 120 may also control a moving speed of the FOV window by dividing a magnitude section of FIG. 2B into subsections. The subsections may range from a "minimum" magnitude section in which an EMG signal is not obtained to a "maximum" magnitude section in which an EMG signal having the greatest magnitude is obtained. As another example, in FIG. 2B, the display controller 120 may divide the magnitude section into subsections such as an "intermediate" magnitude section and a "weak" magnitude section.

FIG. 2C illustrates an example of controlling a moving speed of a FOV window on a map based on the graph of FIG. 2B. Referring to FIG. 2C, the display controller 120 may adjust a speed at which the FOV window moves on the map to be in proportion to a magnitude of an obtained EMG signal. For example, based on a magnitude of an EMG signal, the display controller 120 may control a speed for moving a map area on a display unit. Referring to FIGS. 2B and 2C, when a magnitude of an EMG signal is "minimum," that is, when a strain is not applied to a finger, the display controller 120 may move the FOV window at a speed of "1." As another example, when a magnitude of an EMG signal is "weak," that is, when a weak strain is applied to a finger, the display controller 120 may move the FOV window at a speed of "2," which is a relatively faster speed than the speed of "1."

Similarly, in another example when a magnitude of an EMG signal is "intermediate," that is when an intermediate level of strain is applied to a finger, the display controller 120 may move the FOV window at a speed of "3," which is a relatively faster speed than the speed of "2." The display controller 120 may control the FOV window to move at a speed faster than "3" based on a magnitude of an EMG signal by increasing a distance travelled by the FOV window between the speed of "2" and the speed of "3" to be greater than a distance travelled by the FOV window between the speed of "1" and the speed of "2."

Accordingly, using an EMG signal, the display controller 120 may control a map area belonging to a near area in the entire map to move slowly and may also control a map area belonging to a far area in the entire map to move quickly.

Figure 3A:
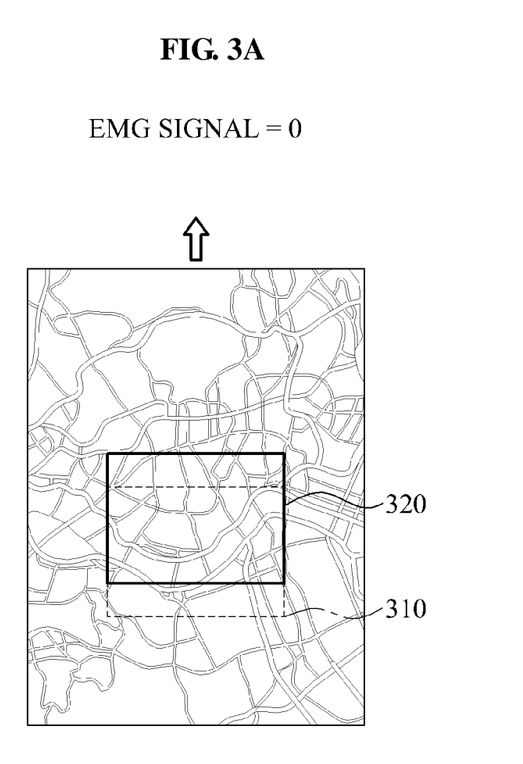
FIGS. 3A through 3C are diagrams illustrating examples of controlling a FOV window to move on a map to be in proportion to a magnitude of an EMG signal.
Figure 3B:
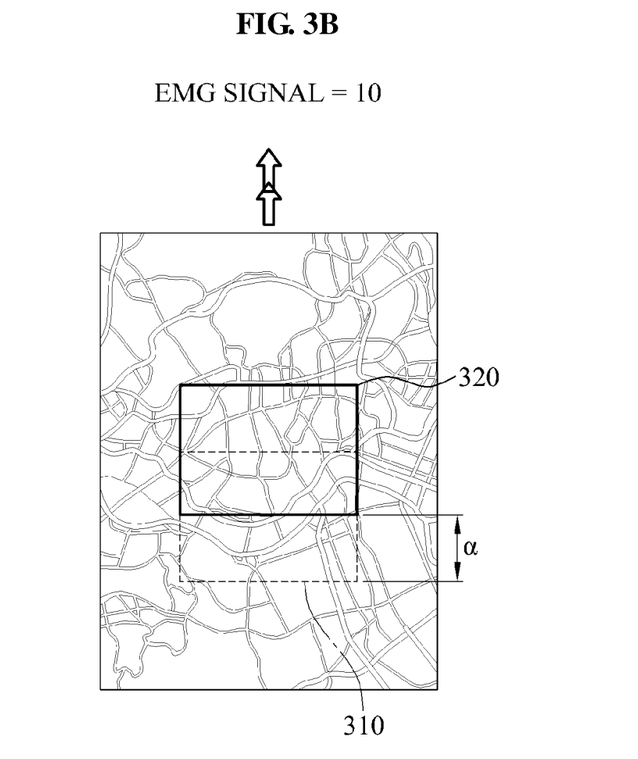
Figure 3C:
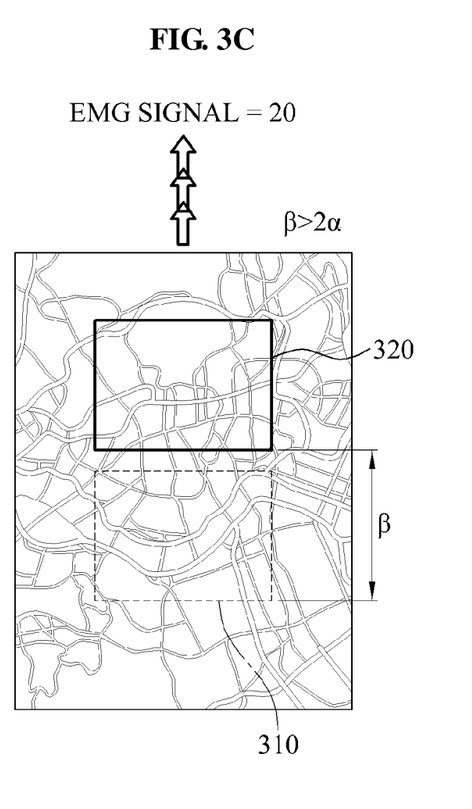

FIGS. 3A through 3C are diagrams illustrating examples of controlling a FOV window's movement on a map to be in proportion to a magnitude of an EMG signal. FIGS. 3A through 3C illustrate examples of displaying a map area on a display unit by different manner of determining a moving speed of a FOV window on a map based on a magnitude of an EMG signal. A dotted line 310 may denote a first map area that is currently displayed on the display unit by the FOV window, and a solid line 320 may denote a second map area, which is not currently displayed on the display unit, but is to be displayed in response to movement of the FOV window.

FIG. 3A illustrates an example in which the display controller 120 moves the FOV window from a first map area 310 to a second map area 320 if "EMG signal=0," which indicates that the EMG signal is not measured from the measurement target 105 and thus, a magnitude of the EMG is "minimum." The display controller 120 may analyze "EMG signal=0" as having a "minimum" magnitude and may control the FOV window to move at a predetermined speed for "minimum" magnitude, for example, a speed of "1."

FIG. 3B illustrates an example in which the display controller 120 moves the FOV window from the first map area 310 to the second map area 320 if "EMG signal=10," which indicates that an EMG signal having a weak magnitude is measured from the measurement target 105. The display controller 120 may analyze "EMG signal=10" as having a "weak" magnitude and may control the FOV window to move at a speed predetermined for "weak" magnitude, for example, a speed of "2."

FIG. 3C illustrates an example in which the display controller 120 moves the FOV window from the first map area 310 to the second map area 320 if "EMG signal=20," which indicates that an EMG signal having an intermediate magnitude is measured from the measurement target 105. The display controller 120 may analyze "EMG signal=20" as having an "intermediate" magnitude and may control the FOV window to move at a speed predetermined for "intermediate" magnitude, for example, a speed of "3."

In FIG. 3C, if "EMG signal=20," a travel distance of the FOV window on the map may be "β." In this example, β may be set to be greater than two folds the travel distance "α" of FIG. 3B (i.e., β>2α). For example, even though a magnitude of an EMG signal increases by two folds, from "10" to "20," the display controller 120 may control the travel distance of the FOV window to be greater than two folds.

The display controller 120 may control the FOV window to move to a farther map area quickly based on a magnitude of an EMG signal by adjusting a moving speed of the FOV window. The display controller 120 may adjust the moving speed of the FOV window associated with the second map area 320, which is not currently displayed on the display unit. to be greater than a moving speed of the FOV window associated with the first map area 310, which is currently displayed on the display unit.

Referring again to FIG. 1, the presentation device 100 may further consider a motion of the measurement target 105 in the case of controlling the FOV window. To this end, the presentation device 100 may further include the second sensor unit 130 configured to obtain an acceleration signal by sensing a motion of the measurement target 105.

The second sensor unit 130 serves to monitor a motion of the measurement target 105 and to verify a direction that is intended or desired to be controlled by a user based on the monitored motion. The second sensor unit 130 may identify a gesture associated with the measurement target 105 based on the sensed motion of the measurement target 105 and obtain an acceleration signal in association with the identified gesture. The second sensor unit 130 may be a sensor, such as, for example, a gyro sensor, a magnetometer, a geomagnetic field sensor, a GPS sensor, and an accelerometer to obtain a signal about a motion of the measurement target 105. In one non-exhaustive example shown in FIG. 1, the second sensor unit 130 and the first sensor unit 110 may be disposed in a bracelet member, which is attached to the measurement target 105.

For example, in response to an upward motion of an arm corresponding to the measurement target 105, the second sensor unit 130 may obtain an acceleration signal associated with the upward motion of the arm. The display controller 120 may move the FOV window in a direction identified by the obtained acceleration signal, at the adjusted moving speed. FIGS. 3A through 3C illustrate examples where the FOV window adjusted at three different moving speeds move "upward" in a direction identified by the acceleration signal. Accordingly, even though a motion range of an arm is limited in searching a map using a wearable mobile device, the presentation device 100 may quickly move the FOV window to a desired area on the map by adjusting a level of an acceleration signal.

The presentation device 100 enables a map search on a distant area of the map to be more efficiently performed by controlling the FOV window to quickly move to a map area belonging to the distant area on the map. The presentation device 100 also enables a more detail map search to be performed on a area closer to the area currently displayed on the map by controlling the FOV window to move relatively slowly in an area belonging to the closer area on the map.

The presentation device 100 may adjust a speed at which the FOV window changes a zooming of a map to be in proportion to a magnitude of the obtained EMG signal. Utilizing zooming a portion of information displayed on a screen in a graphics user interface (GUI) may be enlarged or reduced. The zooming operation may include a zoom-in operation and a zoom-out operation. The display controller 120 may determine a range of a map area displayed on the screen by zooming in or zooming out the FOV window, or may control a zooming change speed based on the magnitude of the obtained EMG signal. For example, when an EMG signal having a relatively great magnitude is obtained within a short period of time, the display controller 120 may control a zoom-in or zoom-out speed of the FOV window with respect to a predetermined position on a map to increase in proportion to the obtained magnitude. Likewise, when an EMG signal having a relatively small magnitude is obtained over a long period of time, the display controller 120 may control a zoom-in or zoom-out speed of the FOV window with respect to a predetermined position on a map to be maintained in proportion to the obtained magnitude.

The display controller 120 may adjust the level of zoom by changing the speed of the FOV window when displaying the map. For example, in the case of displaying a relatively wide area including a currently displayed map area, the display controller 120 may control a map search on the relatively wide area to be efficiently performed by controlling a zoom-out speed of the FOV window to be changed within a shorter period of time. When displaying more detail of a portion of a currently displayed map area, the display controller 120 may support a detail map search on a relatively narrow area by controlling a zoom-in speed of the FOV window to be changed over a longer period of time.

The second sensor unit 130 may sense the motion of the measurement target 105 and the display controller 120 may increase or decrease a range of the map area determined by the FOV window, based on a direction identified by the acceleration signal obtained at the second sensor unit 130. The range of the map area refers to a size of the map area determined by zooming in or zooming out the FOV window. When the FOV window is zoomed out, the size of the map area may become wide. When the FOV window is zoomed in, the size of the map area may become narrow. The display controller 120 may control the FOV window by further considering the motion of the measurement target 105. For example, in response to an upward motion of an arm corresponding to the measurement target 105, the display controller 120 may support a map search on a relatively wide area by moving the FOV window "upward" at a zooming change speed that is adjusted based on the magnitude of the EMG signal. As another example, in response to a downward motion of an arm corresponding to the measurement target 105, the display controller 120 may support a detail map search on a relatively narrow area by moving the FOV window "downward" at a zooming change speed that is adjusted based on the magnitude of the EMG signal.

Figure 4:
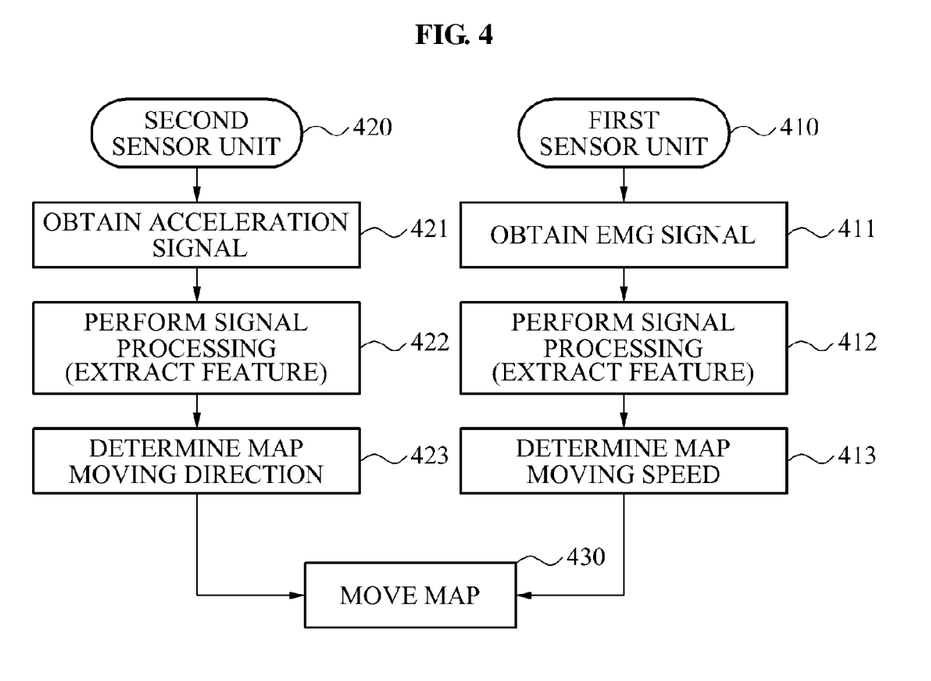
FIG. 4 is a diagram illustrating an example of controlling a FOV window using an EMG signal and an acceleration signal.

FIG. 4 is a diagram illustrating an example of controlling a FOV window using an EMG signal and an acceleration signal. The operations in FIG. 4 may be performed in the sequence and manner as shown, although the order of some operations may be changed or some of the operations omitted without departing from the spirit and scope of the illustrative examples described. Many of the operations shown in FIG. 4 may be performed in parallel or concurrently. The description of FIGS. 1-3C is also applicable to FIG. 4, and thus will not be repeated here.

Referring to FIG. 4, in 411, a first sensor unit 410 that constitutes a presentation device obtains an EMG signal from a measurement target. For example, the first sensor unit 410 may obtain an EMG signal in response to a middle level of strain applied to a wrist that is a measurement target.

In 412, the presentation device extracts a feature by performing signal processing of the EMG signal obtained at the first sensor unit 410. For example, the presentation device may extract the magnitude of the EMG signal as the feature. In this example, the magnitude of the EMG signal may be an "intermediate" magnitude.

In 413, the presentation device determines a map moving speed based on the extracted feature. For example, the presentation device may determine, as the map moving speed, a moving speed of "3" of a FOV window corresponding to the "intermediate" magnitude.

In 421, a second sensor unit 420 that constitutes the presentation device obtains an acceleration signal by sensing a motion of the measurement target. For example, the second sensor unit 420 may obtain an acceleration signal in response to a wrist of the measurement target moving forward.

In 422, the presentation device extracts a feature by performing signal processing of the acceleration signal obtained at the second sensor unit 420. For example, the presentation device may extract a direction identified by the acceleration signal as the feature. In this example, the direction identified by the acceleration signal may be "upward."

In 423, the presentation device determines a map moving direction based on the extracted feature. For example, the presentation device may determine a moving direction of the FOV window corresponding to "upward" as the map moving direction.

In 430, the presentation device moves a map based on the determined map moving speed and map moving direction.

For example, the presentation device may move the map by moving the FOV window upward at a speed of "3" on the map.

As described above, the presentation device may control the FOV window by using an EMG signal and an acceleration signal.

Figure 5:
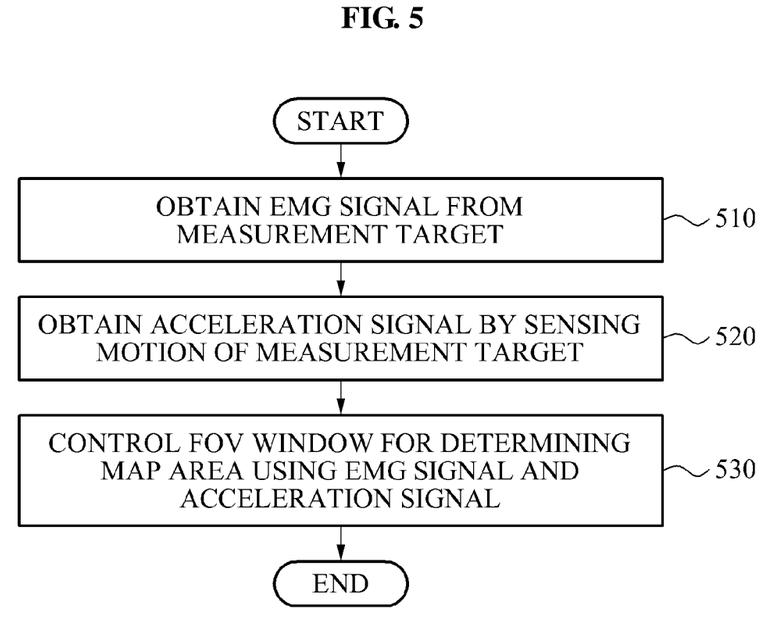
FIG. 5 is a diagram illustrating an example of an operation of a presentation device.

FIG. 5 is a diagram illustrating an example of an operation method of the presentation device 100. The operations in FIG. 5 may be performed in the sequence and manner as shown, although the order of some operations may be changed or some of the operations omitted without departing from the spirit and scope of the illustrative examples described. Many of the operations shown in FIG. 5 may be performed in parallel or concurrently. The description of FIGS. 1-4 is also applicable to FIG. 5, and thus will not be repeated here.

In 510, the presentation device 100 obtains an EMG signal from the measurement target 105 using the first sensor unit 110. Operation 510 is a process of sensing an EMG signal generated in response to a muscular contraction or a muscular relaxation of the measurement target 105. As described above, the measurement target 105 may be any portion of a body where muscles for generating an EMG signal are present, such as, for example, wrist, arm, face, leg, head, and neck of the body. The first sensor unit 110 may include at least one sensor to sense an EMG signal from muscles of the measurement target 105 and may monitor the contraction or relaxation of muscles using the at least one sensor.

In 520, the presentation device 100 obtains an acceleration signal by sensing a motion of the measurement target 105 using the second sensor unit 130.

The second sensor unit 130 serves to monitor a motion of the measurement target 105 and to verify a direction that is intended or desired to be controlled by a user based on the monitored motion. The second sensor unit 130 may identify a gesture associated with the measurement target 105 based on the sensed motion of the measurement target 105 and obtain an acceleration signal in association with the identified gesture.

In one non-exhaustive example shown in FIG. 1, the second sensor unit 130 and the first sensor unit 110 may be disposed in a bracelet member, which is attached to the measurement target 105.

In 530, the presentation device 100 controls a FOV window for determining a map area to be displayed on a display unit using an EMG signal. The FOV window may be a virtual frame used to designate a map area to be displayed on a display unit. In 530, the presentation device 100 may determine the map area to be displayed on the screen by navigating the FOV window on the map.

For example, the presentation device 100 may adjust a speed at which the FOV moves on the map, to be in proportion to a magnitude of the obtained EMG signal. When an EMG signal having a relatively larger magnitude is obtained within a short period of time, the presentation device 100 may control the FOV window to move quickly on the map in proportion to the magnitude of the obtained EMG signal. When an EMG signal having a relatively smaller magnitude is obtained over a long period of time, the presentation device 100 may control the FOV window to move slowly on the map. The movement of the FOV window on the map may be at a predetermined speed.

The presentation device 100 may adjust a moving speed of the FOV window associated with a second map area not currently displayed on the display unit to be greater than a moving speed of the FOV window associated with a first map area currently displayed on the display unit.

For example, the presentation device 100 may control the FOV window to move quickly to the second map area, which is distant from the area currently displayed on the map. Accordingly, a map search on the distant area may be efficiently performed.

The presentation device 100 may control the FOV window to move slowly in a first map, which is closer to an area currently displayed on the map. Accordingly, a detail map search on the near area may be supported.

Also, in 530, the presentation device 100 may move the FOV window in a direction identified by the obtained acceleration signal, at the adjusted moving speed.

The presentation device 100 may also adjust a speed at which the FOV window changes a zooming of a map to be in proportion to a magnitude of the obtained EMG signal. Utiliing zooming a portion of information displayed on a screen in a GUI may be enlarged or reduced. The zooming operation may include a zoom-in operation and a zoom-out operation.

The presentation device 100 may determine a range of a map area displayed on the screen by zooming in or zooming out the FOV window, or may control a zooming change speed based on the magnitude of the obtained EMG signal.

For example, when an EMG signal having a relatively great magnitude is obtained within a short period of time, the presentation device 100 may control a zoom-in or zoom-out speed of the FOV window with respect to a predetermined position on a map to increase in proportion to the obtained magnitude. Likewise, when an EMG signal having a relatively small magnitude is obtained over a long period of time, the presentation device 100 may control a zoom-in or zoom-out speed of the FOV window with respect to a predetermined position on a map to be maintained at a predetermined low speed.

Here, the presentation device 100 may adjust the level of zooming by changing the speed of the FOV window when displaying the map. For example, in the case of displaying a relatively wide area including a currently displayed map area, the presentation device 100 may adjust a zooming change speed of the FOV window in the case of displaying a map may control a map search for the relatively wide area to be efficiently performed by controlling a zoom-out speed of the FOV window to be changed within a shorter period of time.

When displaying more detail of a portion of a currently displayed map area, the presentation device 100 may adjust a zooming change speed of the FOV window in the case of displaying a map may support a detail map search on a relatively narrow area by controlling a zoom-in speed of the FOV window to be changed over a longer period of time.

The second sensor unit 130 may sense the motion of the measurement target 105, and the presentation device 100 may increase or decrease a range of the map area determined by the FOV window, based on a direction identified by the acceleration signal obtained at the second sensor unit 130. The range of the map area refers to a size of the map area determined by zooming in or zooming out the FOV window. When the FOV window is zoomed out, the size of the map area may become wide. When the FOV window is zoomed in, the size of the map area may become narrow.

The presentation device 100 may control the FOV window by further considering the motion of the measurement target 105.

For example, in response to an upward motion of an arm corresponding to the measurement target 105, the presentation device 100 may support an map search on a relatively wide area by moving the FOV window "upward" at a zooming change speed that is adjusted based on the magnitude of the EMG signal.

As another example, in response to a downward motion of an arm corresponding to the measurement target 105, the presentation device 100 may support a detail map search on a relatively narrow area by moving the FOV window "downward" at a zooming change speed that is adjusted based on the magnitude of the EMG signal.

Accordingly, even though a range of motion of an arm is limited in searching a map using a wearable mobile device, the presentation device 100 may quickly move the FOV window to a desired area on the map by adjusting a level of an acceleration signal.

Also, the presentation device 100 enables a map search for an area distant from the area currently displayed on the map to be performed more efficiently by controlling the FOV window to be moved quickly to an area distant from the area currently displayed on the map.

Also, the presentation device 100 enables a map search for a near area to be performed more in detail by controlling the FOV window to move relatively slowly in the area belonging to the near area on a map.

The processes, functions, and methods described above including a method for beamforming can be written as a computer program, a piece of code, an instruction, or some combination thereof, for independently or collectively instructing or configuring the processing device to operate as desired. Software and data may be embodied permanently or temporarily in any type of machine, component, physical or virtual equipment, computer storage medium or device that is capable of providing instructions or data to or being interpreted by the processing device. The software also may be distributed over network coupled computer systems so that the software is stored and executed in a distributed fashion. In particular, the software and data may be stored by one or more non-transitory computer readable recording mediums. The non-transitory computer readable recording medium may include any data storage device that can store data that can be thereafter read by a computer system or processing device. Examples of the non-transitory computer readable recording medium include read-only memory (ROM), random-access memory (RAM), Compact Disc Read-only Memory (CD-ROMs), magnetic tapes, USBs, floppy disks, hard disks, optical recording media (e.g., CD-ROMs, or DVDs), and PC interfaces (e.g., PCI, PCI-express, WiFi, etc.). In addition, functional programs, codes, and code segments for accomplishing the example disclosed herein can be construed by programmers skilled in the art based on the flow diagrams and block diagrams of the figures and their corresponding descriptions as provided herein.

The apparatuses and units described herein may be implemented using hardware components. The hardware components may include, for example, controllers, sensors, processors, generators, drivers, and other equivalent electronic components. The hardware components may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The hardware components may run an operating system (OS) and one or more software applications that run on the OS. The hardware components also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a hardware component may include multiple processors or a processor and a controller. In addition, different processing configurations are possible, such a parallel processors.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A presentation device, comprising:
   a first sensor unit configured to contact a measurement target and to obtain an electromyographic (EMG) signal from the measurement target; and
   a display controller configured to control a field of view (FOV) window for displaying a map area based on the EMG signal,
   wherein the display controller is further configured to
      control the FOV window to move on the map in proportion to the magnitude of the obtained EMG signal upon determining that the EMG signal is obtained within a short period of time,
      control the FOV window to move on the map at a predetermined low speed upon determining that the EMG signal is obtained over a long period of time,
      adjust a speed of the FOV window associated with a second map area that does not include the displayed map area to be greater than a speed of the FOV window associated with the displayed map area, and
      control the FOV to move on the map at a predetermined minimum speed, when a strain is not applied to a finger.

2. The presentation device of claim 1, further comprising:
   a second sensor unit configured to obtain an acceleration signal by sensing a motion of the measurement target,
   wherein the display controller is configured to move the FOV window toward a direction identified by the acceleration signal.

3. The presentation device of claim 1, wherein the display controller is configured to adjust a zooming speed of the FOV window in response to a magnitude of the obtained EMG signal.

4. The presentation device of claim 3, wherein the display controller is configured to adjust a zooming speed of the FOV window associated with displaying a map area that includes the displayed map area to be greater than a zooming speed of the FOV window associated with displaying a portion of the displayed map area.

5. The presentation device of claim 3, further comprising:
   a second sensor unit configured to obtain an acceleration signal by sensing a motion of the measurement target,
   wherein the display controller is configured to increase or decrease a size of a map area associated with the FOV window, based on a direction identified by the acceleration signal.

6. The presentation device of claim 1, wherein the first sensor unit is configured to obtain the EMG signal generated in response to at least one of a muscular contraction or a muscular relaxation of the measurement target.

7. The presentation device of claim 1, wherein the map area is displayed on a display unit.

8. The presentation device of claim 1, wherein the electromyographic (EMG) signal includes one or more of a bioelectric/magnetic signal, a bio-impedance signal, and a biomechanical signal.

9. The presentation device of claim 1, wherein the first sensor unit contacts the wrist of the measurement target.

10. The presentation device of claim 9, wherein the first sensor unit contacts the wrist of the measurement target by surrounding the entire wrist; and
    wherein the first sensor is spread throughout the wrist.

11. The presentation device of claim 1, wherein the display controller is configured to control multiple separate logical displays permitting different content to be displayed on the logical displays.

12. The presentation device of claim 1, wherein the magnitude of the obtained EMG signal is divided into subsections.

13. A method of operating a presentation device, the method comprising:
    obtaining an electromyographic (EMG) signal from a measurement target using a first sensor unit in contact with the measurement target; and
    controlling a field of view (FOV) window to determine a map area to be displayed based on the EMG signal,
    wherein the controlling the FOV window comprises
       controlling the FOV window to move on the map in proportion to the magnitude of the obtained EMG signal upon determining that the EMG signal is obtained within a short period of time,
       controlling the FOV window to move on the map at a predetermined low speed upon determining that the EMG signal is obtained over a long period of time,
       controlling the FOV window by adjusting a speed of the FOV window associated with a second map area that does not include the displayed map area to be greater than a speed of the FOV window associated with the displayed map area, and
       controlling the FOV window to move on the map at a predetermined minimum speed, when a strain is not applied to a finger.

14. The method of claim 13, further comprising:
    obtaining an acceleration signal by sensing a motion of the measurement target, using a second sensor unit,
    wherein the controlling the FOV window comprises controlling the FOV window by moving the FOV window toward a direction identified by the acceleration signal.

15. The method of claim 13, wherein the controlling the FOV window comprises controlling the FOV window by adjusting a zooming speed of the FOV window in response to a magnitude of the obtained EMG signal.

16. The method of claim 15, wherein the controlling the FOV window comprises controlling the FOV window by adjusting a zooming speed of the FOV window associated with displaying a map area that includes the displayed map area to be greater than a zooming speed of the FOV window associated with displaying a portion of the displayed map area.

17. The method of claim 15, further comprising:
obtaining an acceleration signal by sensing a motion of the measurement target, using a second sensor unit,
wherein the controlling the FOV window comprises controlling the FOV window by increasing or decreasing a size of a map area associated with the FOV window based on a direction identified by the acceleration signal.

18. A presentation device, comprising:
a first sensor unit configured to contact a measurement target and to obtain an electromyographic (EMG) signal from the measurement target;
a second sensor unit configured to obtain an acceleration signal by sensing a motion of the measurement target; and
a display controller configured to control a field of view (FOV) window for displaying a map area based on at least one of the EMG signal or a direction identified by the acceleration signal,
wherein the display controller is further configured to
control the FOV window to move on the map in proportion to the magnitude of the obtained EMG signal upon determining that the EMG signal is obtained within a short period of time,
control the FOV window to move on the map at a predetermined low speed upon determining that the EMG signal is obtained over a long period of time,
adjust a speed of the FOV window associated with a second map area that does not include the displayed map area to be greater than a speed of the FOV window associated with the displayed map area, and
control the FOV window to move on the map at a predetermined minimum speed, when a strain is not applied to a finger.

19. The presentation device of claim 18, wherein the display controller is configured to control the FOV window to display a second map area that is greater than the displayed map area in response to a upward motion of the measurement target.

20. The presentation device of claim 18, wherein the display controller is configured to control the FOV window to display a second map area that is smaller than the displayed map area in response to a downward motion of the measurement target.

21. The presentation device of claim 18, wherein the presentation device is a mobile device.

22. The presentation device of claim 21, wherein the mobile device comprises a display unit configured to display the map area.

23. The presentation device of claim 18, wherein the presentation device is a wearable smart device.

* * * * *